(12) United States Patent
Sherman et al.

(10) Patent No.: US 7,699,879 B2
(45) Date of Patent: Apr. 20, 2010

(54) APPARATUS AND METHOD FOR PROVIDING DYNAMIZABLE TRANSLATIONS TO ORTHOPEDIC IMPLANTS

(75) Inventors: Michael C. Sherman, Memphis, TN (US); Jeff R. Justis, Collierville, TN (US)

(73) Assignee: Warsaw Orthopedic, Inc.

( * ) Notice: Subject to any disclaimer, the term of this patent is extended or adjusted under 35 U.S.C. 154(b) by 886 days.

(21) Appl. No.: 10/689,961

(22) Filed: Oct. 21, 2003

(65) Prior Publication Data

US 2005/0085812 A1   Apr. 21, 2005

(51) Int. Cl.
 *A61B 17/80* (2006.01)
(52) U.S. Cl. .................................. 606/289; 606/908
(58) Field of Classification Search ............... 606/61, 606/69, 70, 71, 62–68, 60, 246, 257, 267, 606/280–282, 286, 288–289, 76–77, 907–910; 623/23.75, 23.58, 23.59; 424/422, 423
See application file for complete search history.

(56) References Cited

U.S. PATENT DOCUMENTS

| | | | |
|---|---|---|---|
| 2,987,062 A | 6/1961 | Ellison | |
| 4,279,249 A | 7/1981 | Vert et al. | |
| 4,338,926 A * | 7/1982 | Kummer et al. | ............... 606/70 |
| 4,356,572 A * | 11/1982 | Guillemin et al. | ......... 623/23.61 |
| 4,512,038 A | 4/1985 | Alexander et al. | |
| 4,539,981 A | 9/1985 | Tunc | |
| 4,550,449 A | 11/1985 | Tunc | |
| 4,655,203 A | 4/1987 | Tormala et al. | |
| 4,743,257 A | 5/1988 | Toermaelae et al. | |
| 4,756,307 A | 7/1988 | Crowninshield | |
| 4,773,406 A | 9/1988 | Spector et al. | |
| 4,781,183 A | 11/1988 | Casey et al. | |
| 4,905,680 A | 3/1990 | Tunc | |
| 5,013,315 A | 5/1991 | Barrows | |
| 5,057,111 A | 10/1991 | Park | |
| 5,085,661 A * | 2/1992 | Moss | .......................... 606/139 |
| 5,092,884 A | 3/1992 | Devereux et al. | |
| 5,108,755 A | 4/1992 | Daniels et al. | |
| 5,261,911 A | 11/1993 | Carl | |

(Continued)

FOREIGN PATENT DOCUMENTS

DE     200 01 879 U1    3/2000

(Continued)

OTHER PUBLICATIONS

Vert M: "Les Materiaux Bioresorbables" Cahiers D'Enseignement de la Sofcot, Expansion Scientifiques Francaise, FR, Jan. 1986, pp. 83-89, XP000606083.

(Continued)

*Primary Examiner*—Thomas C Barrett
*Assistant Examiner*—James L. Swiger

(57) ABSTRACT

The present invention generally relates to orthopedic devices and methods for treating bone defects. The orthopedic devices can provide sufficient support to the bone defect while allowing bone ingrowth and minimizing the risk to stress shield and/or pseudo-arthrodesis. The bone fixation devices include a biodegradable material or component that further resists relative motion of attached bones and allows the device to gradually transfer at least some load from the device to the growing bone structure in vivo and permitting an increase in the relative motion of bones attached to the device.

16 Claims, 8 Drawing Sheets

U.S. PATENT DOCUMENTS

| | | | |
|---|---|---|---|
| 5,458,653 A | 10/1995 | Davidson | |
| 5,514,137 A | 5/1996 | Coutts | |
| 5,522,895 A * | 6/1996 | Mikos | 623/23.58 |
| 5,591,169 A | 1/1997 | Benoist | |
| 5,658,343 A | 8/1997 | Haeuselmann et al. | |
| 5,725,591 A | 3/1998 | DeCarlo, Jr. et al. | |
| 5,733,287 A * | 3/1998 | Tepic et al. | 606/280 |
| 5,733,338 A | 3/1998 | Kampner | |
| 5,735,901 A | 4/1998 | Maumy et al. | |
| 5,779,706 A | 7/1998 | Tschakaloff | |
| 5,824,088 A | 10/1998 | Kirsch et al. | |
| 5,902,599 A | 5/1999 | Anseth et al. | |
| 5,935,127 A * | 8/1999 | Border | 606/62 |
| 5,935,172 A | 8/1999 | Ochoa et al. | |
| 6,004,323 A | 12/1999 | Park et al. | |
| 6,013,104 A | 1/2000 | Kampner | |
| 6,017,366 A | 1/2000 | Berman | |
| 6,019,792 A | 2/2000 | Cauthen | |
| 6,027,742 A | 2/2000 | Lee et al. | |
| 6,045,579 A | 4/2000 | Hochshuler et al. | |
| 6,080,193 A | 6/2000 | Hochshuler et al. | |
| 6,160,084 A | 12/2000 | Langer et al. | |
| 6,179,874 B1 | 1/2001 | Cauthen | |
| 6,187,008 B1 | 2/2001 | Hamman | |
| 6,206,883 B1 | 3/2001 | Tunc | |
| 6,214,008 B1 | 4/2001 | Illi | |
| 6,232,384 B1 | 5/2001 | Hyon | |
| 6,241,771 B1 | 6/2001 | Gresser et al. | |
| 6,293,949 B1 * | 9/2001 | Justis et al. | 606/61 |
| 6,296,645 B1 * | 10/2001 | Hover et al. | 606/62 |
| 6,413,259 B1 * | 7/2002 | Lyons et al. | 606/69 |
| 6,540,746 B1 | 4/2003 | Buhler et al. | |
| 6,605,090 B1 | 8/2003 | Trieu et al. | |
| 6,786,908 B2 * | 9/2004 | Hover et al. | 606/62 |
| 6,808,527 B2 * | 10/2004 | Lower et al. | 606/62 |
| 6,945,973 B2 * | 9/2005 | Bray | 606/61 |
| 2002/0103488 A1 | 8/2002 | Lower et al. | |
| 2003/0191470 A1 | 10/2003 | Ritland | |
| 2003/0195515 A1 | 10/2003 | Sohngen | |

FOREIGN PATENT DOCUMENTS

| | | |
|---|---|---|
| WO | WO 86/00533 A | 1/1986 |
| WO | WO 03/043486 A | 5/2003 |
| WO | WO 2004/110290 A | 12/2004 |

OTHER PUBLICATIONS

Coffey A B et al., "Development of thin-walled fibre-reinforced structures for medical applications", Composites Part A: Applied Science and Manufacturing, Elsevier Science Publishers B.V., Amsterdam, NL, vol. 34, No. 6, Jun. 2003, pp. 535-542.

Slosarczyk A et al., "Hot pressed hydroxyapatite-carbon fibre composites", Journal of the European Ceramic Society, Elsevier Science Publishers, Barking, Essex, GB, vol. 20, No. 9, Aug. 2000, pp. 1397-1402.

Hudgins R Garryl et al., "Assessment of compressive strength of flexible composite materials for spinal implantation", Journal of Composite Materials, vol. 34, No. 17, 2000, pp. 1472-1493.

* cited by examiner

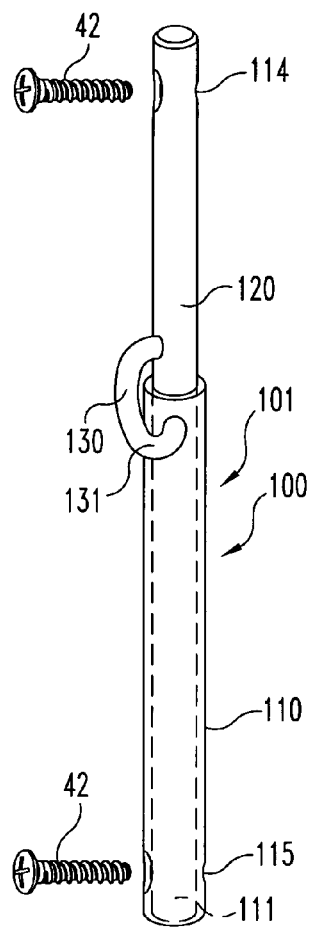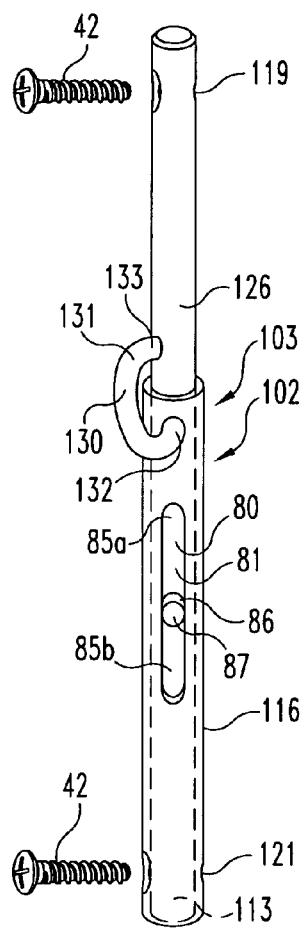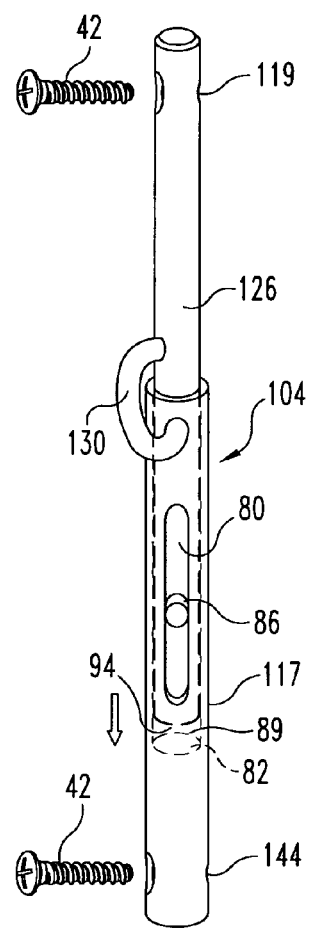
*Fig. 3a*  *Fig. 3b*  *Fig. 3c*

APPARATUS AND METHOD FOR PROVIDING DYNAMIZABLE TRANSLATIONS TO ORTHOPEDIC IMPLANTS

FIELD OF THE INVENTION

The present invention relates generally to orthopedic devices for promoting bone fusion and methods for treating orthopedic defects using the orthopedic devices.

BACKGROUND OF THE INVENTION

The spine is composed of both rigid and flexible elements which form a complex structure that can readily accommodate a wide range of motions and adjust to a wide range of loads. Unfortunately, like any complex physiological structure, the spine is also vulnerable to disease, injury, and congenital deficiencies, all of which can cause defects to the spine and, in particular, to the vertebral body and intervertebral discs. Spinal disease, injury, and deformity may have a disastrous impact on patient well being, ranging from acute pain to chronic debilitating pain and, in the most severe cases, partial or complete paralysis.

Some of the most common pathologies of spinal defects include fractured, diseased, or decayed vertebral bodies; torn or stretched ligaments; and damaged or diseased intervertebral discs.

Common treatments for damaged, diseased, or defective vertebrae include joining or fusing fractured bone segments or portions together to stabilize the affected parts and removing the affected vertebrae, either in part or in whole. Classically, the damaged disc is excised, the adjacent vertebrae are mechanically joined together, and oftentimes bone is grafted into the region, particularly in the disc space between the two vertebrae, to promote fusion of the adjacent vertebrae. The vertebrae can be mechanically joined using a prosthetic device such as a bone plate that is attached to the adjacent vertebrae with bone screws. The bone plate eliminates disparate motion between the two bone portions to allow arthrodesis.

It is known that for load bearing bone members, stronger, denser bone tissue results when new bone growth occurs under pressure and that the risk of a weakened juncture or pseudoarthrodesis increases when a prosthetic device stress shields new bone growth. The problem arises of when and how much pressure or force to apply to develop a strong junction between the bone portions. The bone portions should be secured and supported during initial bone growth. However, the optimum support necessary for desired bone growth may vary over time as the bony juncture or bridge develops between the bone portions.

Similarly, torn and/or structural ligaments can be treated by initially securing/immobilizing the ligaments. This can be accomplished using internal and/or external prosthetic devices to augment or replace the stability lost as a result of the damaged ligaments. Further, the treated ligaments can be susceptible to repeated injury. Consequently, it may be desirable to augment the treated ligament by implanting a prosthesis or device that allows limited movement of the affected ligaments, i.e., stretching and rotation of the ligaments. Current treatment methods do not allow for an implanted device to initially secure/immobilize the ligaments and then allow limited movement of the same without a subsequent surgical revisitation.

In light of the above, there is a continuing need for devices and treatments that stabilize and support damaged bone tissue, bony structures, and connecting tissue and provide variable loads to growing bone as well as a measure of flexible support to injury- or disease-prone bones and connecting tissue. The present invention addresses this need and provides other benefits and advantages in a novel and nonobvious manner.

BRIEF SUMMARY OF THE INVENTION

The present invention relates to orthopedic devices and the manufacture and use thereof. Various aspects of the invention are novel, nonobvious, and provide various advantages. While the actual nature of the invention covered herein can only be determined with reference to the claims appended hereto, certain forms and features, which are characteristic of the preferred embodiments disclosed herein, are described briefly as follows.

In one form, the present invention provides an orthopedic device for securing two or more bone portions. The orthopedic device comprises: an elongate member including a receptacle therein and configured to be fixedly secured to two or more bone portions allowing translational, or rotational, or both translational and rotational movement of a first one of the bone portions relative to a second one of the bone portions; and a restricting component comprising a biodegradable material and disposed in the receptacle to inhibit the translational, the rotational, or both the translational and rotational movement of the first of the bone portions relative to the second of the bone portions.

The orthopedic device can be used to treat a variety of bone defects including but not limited to: bone fractures, diseased bone tissue, spinal diseases, diseased/damaged vertebrae, torn or stretched ligaments, and the like.

In preferred embodiments, the device prevents stress shielding of new, developing bone tissue. In other embodiments, the orthopedic device of the present invention can be configured for articulating joints. In these embodiments, the device can allow a limited amount of movement, i.e. translation and/or rotation about the joint. The devices, with and without the biodegradable component, still provide a measure of support and/or restriction of the movement of bone portions attached to the device. In preferred embodiments, the devices of the present invention remain in place indefinitely.

In another form, the present invention provides a device for securing bone portions. The device can comprise: a body member comprising a first arm and an opposite second arm defining a receptacle therebetween; an elongate rod disposed within the receptacle; a restricting component comprising a biodegradable material and disposed within the receptacle; and a cap configured to engage the first and second arms and secure the rod and the bioabsorbable restricting component in the receptacle.

In still other forms, the present invention provides a method for treating a bone defect. The method comprises: providing an orthopedic device that includes an elongate member having at least one receptacle therein and a restricting component disposed within the at least one receptacle. The restricting component is composed of a biodegradable material. The method further includes securing the elongate member to a first bone portion with a first fastener and to a second bone portion with a second fastener to restrict translational or rotational movement or both the translational and rotational movement of the first bone portion relative to the second bone portion. The secured device can support and effectively immobilize the two bone portions relative to each other. In vivo, the biodegradable material can degrade and, consequently, allow translational or rotational movement or both translational and rotational movement of the first bone portion relative to the second bone portion. Preferably the elongate member remains secured to the first and second bone portions. The degradation of the biodegradable material can occur over time. This effectively transfers at least a portion of the support and/or biomechanical load from the elongate device to the new bone growth at the treatment site.

Further objects, features, aspects, forms, advantages, and benefits shall become apparent from the description and drawings contained herein.

BRIEF DESCRIPTION OF THE DRAWINGS

FIG. 3a is a perspective view of one embodiment of an orthopedic device having telescoping elongate members joined by a loop of material in accordance with the present invention.

FIG. 3b is a perspective view of another embodiment of an orthopedic device having telescoping elongate members joined by a loop of material in accordance with the present invention.

FIG. 3c is a perspective view of still another embodiment of an orthopedic device having telescoping elongate members joined by a loop of material in accordance with the present invention.

DESCRIPTION OF THE PREFERRED EMBODIMENTS

Figure 1A:
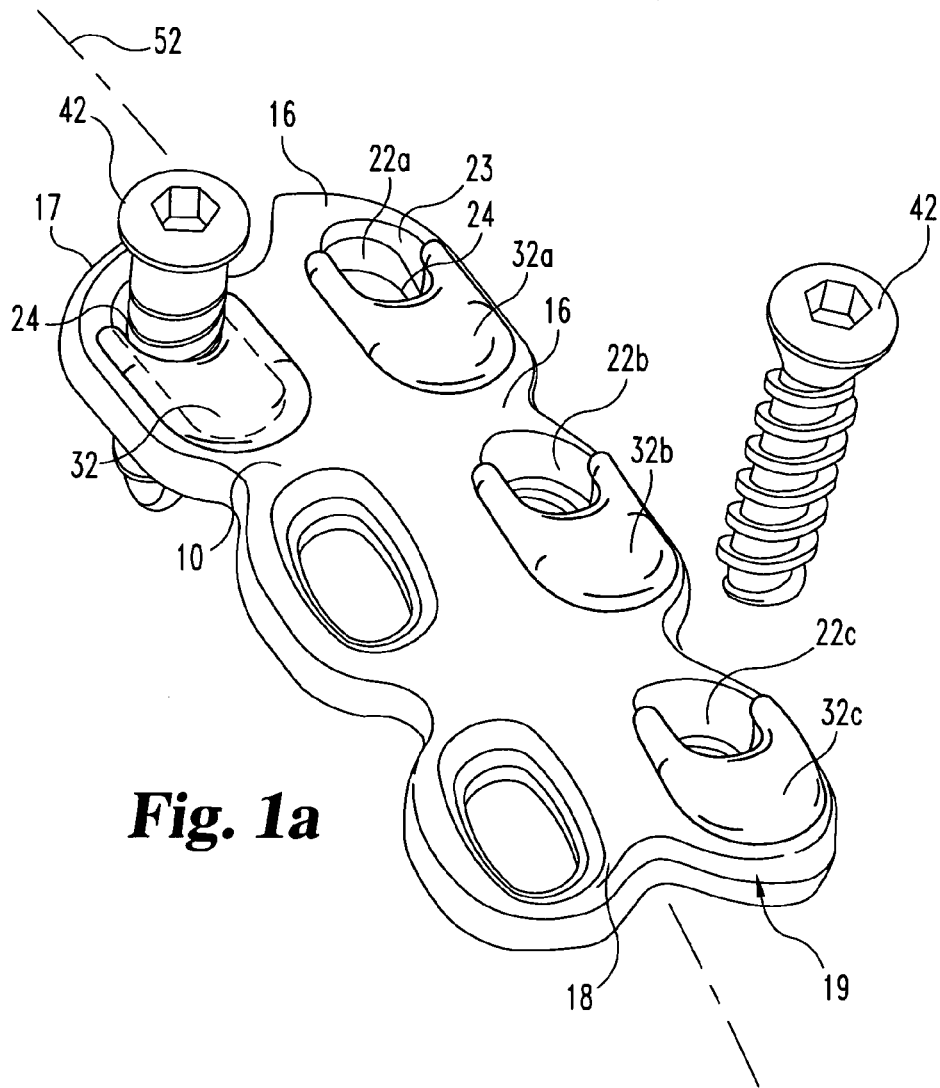
FIG. 1a is a perspective view of one embodiment of a bone fixation device comprising an elongate member in the form of a bone plate in accordance with the present invention.

For the purposes of promoting an understanding of the principles of the invention, reference will now be made to the embodiments illustrated herein, and specific language will be used to describe the same. It will nevertheless be understood that no limitation of the scope of the invention is thereby intended. Any alterations and further modifications in the described devices, systems, and treatment methods, and any further applications of the principles of the invention as described herein, are contemplated as would normally occur to one skilled in the art to which the invention relates.

In preferred embodiments, the present invention provides an implantable orthopedic device or prosthesis to facilitate support and repair of defective bone structures and/or connective tissue. The defective bone structures can be the result of damaged, traumatized, and/or diseased tissue. By use of the term "orthopedic device", it is intended to include within its meaning a device that can be used to treat or repair defective, diseased, and/or damaged tissue of the muscular/skeletal system(s).

The devices of the present invention can provide initial support and/or fixation of selected bone structures. After a selected period of time or under certain conditions, the amount and nature of the support/fixation can vary to facilitate a desirable treatment. For example, use of a device according to the present invention that allows the variable or dynamizable support develops new, strong bone tissue, thus minimizing the risk of pseudoarthrodesis.

The biodegradable component of the present invention provides a restricting component for the inventive device. This restricting component can provide rigidity and support for both the implanted orthopedic fusion device and, consequently, the attached bone structures. In use, the load supported by the bone fixation device and supported by the restricting component can vary. This allows the fixation device to become dynamizable, or change its support characteristics in vivo. This change in support characteristics can be particularly important for developing strong, new bone tissue at the bone defection or fusion site. This prevents stress shielding of the new bone ingrowth and minimizes the risk for the development of pseudoarthrodesis.

The devices of the present invention also find advantageous use in the treatment of connecting tissue such as ligaments. The devices can augment the connecting tissue. After a predetermined period of time or condition, the device can allow limited movement, either translational or rotational or both translational and rotational, of the connecting tissue and/or attached bone structures as desired. For example, if the natural connecting tissue is elastic, the device can serve to limit or restrict the overall length or amount that the connecting tissue stretches. This restriction can vary depending upon the length of time or preselected conditions in forming and using the device. The following description specifically describes non-limiting, specific embodiments for use with the present invention.

It should be understood that other configurations can be used which impart the ability of the elongate member to change resistance to translational and/or rotational movement as the biodegradable component of the device biodegrades.

FIG. 1a is a perspective view of one embodiment of an orthopedic device 10 comprising an elongate member 16 defining an elongate axis 52. In the illustrated embodiment, member 16 comprises a bone plate 18. Device 10 can include one receptacle 24 or a plurality of receptacles 22a, 22b, 22c . . . . Bone fastener 42 can be inserted through receptacle 24 to secure elongate member 16 to one, two, or more bone portions.

In a preferred embodiment, one or more of receptacles 22a, 22b, 22c . . . are sized to have a larger opening than the outer diameter of the threads and/or shank of fastener 42. In this embodiment, member 16 has limited freedom to move while secured to two or more bone portions.

When a first end 17 of member 16 is secured to a first bone portion, and a second end 19 is secured to a second bone portion, the two bone portions are free to move relative to each other and/or member 16.

In one form, receptacles 24, 22a, 22b, 22c . . . are provided as over-sized openings relative to the threads and/or shank of a bone fastener. In other forms, receptacles 24, 22a, 22b, 22c . . . are provided as oblong openings. When provided as oblong openings, they can be oriented with the long dimension of the oval, either parallel with each other or at one or more angles with each other.

Restricting component(s) 32, 32a, 32b, 32c . . . can be disposed in one or more of receptacles 24, 22a, 22b, 22c . . . . It will be understood that in alternative embodiments, each one of receptacles 24, 22a, 22b, 22c . . . need not include restricting component 32, 32a, 32b, 32c . . . respectively. Restricting component 32 is operatively positioned to further inhibit or restrict the motion of bone portions (not shown) attached to device 10. In one embodiment, receptacle 24 has a rim or edge 23. Restricting component 32 can be deposited in receptacle 24 between edge 23 and fastener 42. In other embodiments, restricting component 32 completely surrounds fastener 42. In this embodiment, restricting component 32 can initially fill up or cover over receptacle 24. Fastener 42 can then be inserted through restricting component 32 and receptacle 24. In other embodiments, restricting component 32 can be deposited in receptacle 24 and define an opening therethrough for receiving fastener 42. In one preferred embodiment, restricting component 32 is operatively positioned within receptacle 24 such that restricting component 32 contacts only a portion of the edge 23 of receptacles 22a, 22b, 22c.

Restricting component 32 is operatively positioned within receptacle 24 such that it further restricts the translational and/or rotational motion of attached bone portions. Receptacles 24, 22a, 22b, 22c . . . can be configured to allow or restrict movement of secured bone portions in only one direction, or two or more directions, as desired. Similarly, receptacles 24, 22a, 22b, 22c . . . can be configured to allow either rotation or translation or both, as desired.

Restricting component 32 comprises a biodegradable material, discussed more fully below. In vivo, the biodegrading material degrades. In a preferred embodiment, after restricting component 32 has been eliminated, fastener 42 continues to secure elongate member 16 to attached bone portions. Elongate member 16 continues to provide at least some support to attached bone and to restrict at least some of the translational and/or rotational motion of attached bone portions.

One example of a similar bone plate is disclosed in U.S. Pat. No. 6,152,927, which is incorporated herein by reference in its entirety.

Figure 1B:
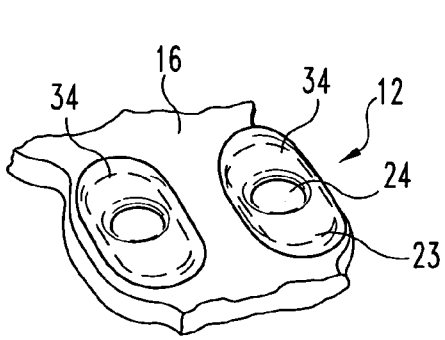
FIG. 1b is a partial, perspective view of another embodiment of a bone fixation device similar to the device of FIG. 1a, illustrating the restricting component symmetrically disposed in the receptacle in accordance with the present invention.

FIG. 1b is a partial, perspective view of another embodiment of an orthopedic device 12. Device 12 is formed similarly to device 10 and, consequently, the same reference numbers are used to denote like components. Device 12 comprises at least one receptacle 24. A restricting component 34 is symmetrically disposed in receptacle 24. In a preferred embodiment, restricting component 34 is placed in contact with the entire rim or edge 23 shown in dashed lines of receptacle 24. Fastener 42 extends through restricting component 34 and can be used to secure elongate member 16 to a portion of bone. When present, restricting component 34 is operatively positioned within device 12 so as to further restrict the motion of bone portions attached to device 12.

Figure 1C:
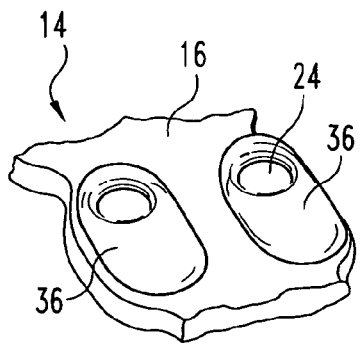
FIG. 1c is a partial, perspective view of still another embodiment of a bone fixation device similar to the device of FIG. 1a, illustrating the restricting component asymmetrically disposed in the receptacle in accordance with the present invention.

FIG. 1c is a partial, perspective view of another preferred embodiment of an orthopedic device 14. Device 14 is formed similarly to device 10 and, consequently, the same reference numbers are used to denote like components. Device 14 comprises at least one receptacle 24. In the illustrated embodiment, restricting component 36 is asymmetrically disposed in receptacle 24.

In embodiments such as those illustrated in FIGS. 1a, 1b, and 1c, elongate member 16 includes more than one feature, for example multiple receptacles 22 fitted with biodegradable restricting component 32, 34, and 36. Elongate member 16 can be secured to at least one portion of bone by a variety of fasteners including bone nails, staples, bone adhesives, bone screws, bone hooks, and the like.

A variety of biodegradable restricting components, both biodegradable and bio-stable, can be used within the same orthopedic device to optimize the change in translational and/or rotational motion of bone portions attached to the devices as the restricting components biodegrade.

Figure 2A:
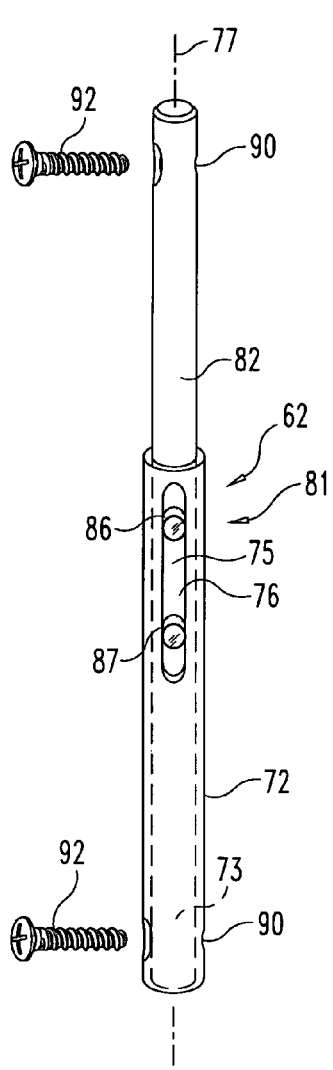
FIG. 2a is a perspective view of one embodiment of an orthopedic device having a two-part telescoping elongate member in accordance with the present invention.

FIG. 2a is a perspective view of one embodiment of an orthopedic device 62 in accordance with the present invention. Device 62 includes an elongate member 81 that comprises an assembly of two or more telescoping rod members. In the illustrated embodiment, elongate member 81 comprises a first rod 72 and a second rod 82. Second rod 82 is slidably received within a lumen 73 of first rod 72. First rod 72 also includes a receptacle 75 formed therein. Receptacle 75 can be sized to accommodate a first restricting component 86.

In the illustrated embodiment, receptacle 75 is illustrated as a slot 76 extending substantially parallel to the elongate axis 77 of first rod 72. In alternative embodiments, receptacle 75 can be provided as a cylindrical opening.

Second rod 82 is slidably received within lumen 73 of first rod 72. In this embodiment, second rod 82, in the absence of a restricting component, can freely move either translational and/or rotational within lumen 73. Additionally, second rod 82 can include one or more openings positioned along its length to be in registry with receptacle 75. One or more restricting components, either 86 or 87, can be inserted through receptacle 75 and into the openings formed in second rod 82, similar to the insertion of a peg in a hole or an opening.

First restricting component 86 is positioned in receptacle 75 to inhibit movement of rod 82 in relationship to rod 72. In preferred embodiments, a second restricting component 87 can be disposed in the same slot 76. It will be understood to those skilled in the art that a plurality of restricting components can be inserted through slot 76 and is intended to be included within the scope of the present invention.

When receptacle 75 is provided as slot 76, the first and second restricting components 86 and 87 can be positioned within slot 76 to initially allow no rotational or translational movement of second rod 82 in relation to first rod 72 (and corresponding to the attached first and second bone portions). In other embodiments, first and second restricting components 86 and 87 can be positioned in slot 76 to allow either limited translational movement of second rod 82 within lumen 73 and/or limited rotational movement of second rod 82 within lumen 73.

First rod 72 and second rod 82 are configured to be secured to a bone defect. For example, first rod 72 can include an opening 90 extending therethrough to receive a fastener 92. In the illustrated embodiment, fastener 92 is illustrated as a bone screw. Similarly, second rod 82 can be provided with opening 91 extending therethrough to receive a fastener 92. In the illustrated embodiment, both first rod 72 and second rod 82 are illustrated as cylindrical, elongate rods. In other embodiments, it will be understood that alternative configurations of first rod 72 and second rod 82 are intended to be included within the scope of the present invention. For example, first and second rods 72 and 82 respectively can be provided to have a square or rectangular cross section. In still other embodiments, first rod 72 can be provided in the form of a "U-shaped" rod defining a channel into which second rod 82 can be received.

One or more of restricting components 86 and 87 can be formed of a biodegradable material as described more fully below. In alternative embodiments, only first restricting component 86 need be composed of the biodegradable material. The second restricting component 87 can be composed of any biocompatible material including biocompatible polymeric materials, metallic materials, and ceramic materials, discussed more fully below.

Figure 2B:
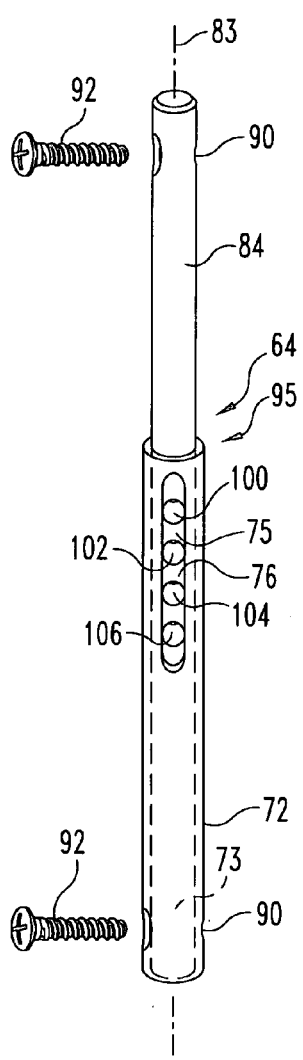
FIG. 2b is a perspective view of another embodiment of an orthopedic device having a two-part telescoping elongate member in accordance with the present invention.

FIG. 2b is a perspective view of another embodiment of an orthopedic device 64. Orthopedic device 64 is formed similarly to device 62 and, consequently, the same reference numbers will be used to denote like components. Device 64 includes an elongate member 95 comprising an assembly of rods 72 and 84. First rod 72 can be provided as has been described for FIG. 2a. Second rod 84 is slidably disposed within lumen 73 of rod 72. Second rod 84 includes a plurality of openings 100, 102, 104, . . . . Each of openings 100, 102, 104 . . . can be sized and positioned about rod 84 to receive a restricting component similar to a peg or plug in an opening. In the illustrated embodiment, the openings 100, 102, 104 . . . are illustrated as being linearly aligned with the elongate axis 83. In other embodiments, openings 100, 102, 104 . . . can be axially displaced and/or radially displaced from each other in second rod 84. Consequently, in still yet alternative embodiments, second rod 84 can be provided as an imperforate rod including a plurality of openings extending therethrough. In this fashion, a surgeon can selectively pick a particular opening or set of openings in which to insert a restricting component. Consequently, the length of device 64 can be varied by selectively using one or more of openings placed around or in second rod 84.

First rod 72 includes receptacle 75, which is illustrated as slot 76. It will also be understood that slot 76 need not extend in the axial direction along first rod 72. In alternative embodiments, slot 76 can be formed as an arc either horizontally or spirally about first rod 72. In still other embodiments, receptacle 75 can be provided as a round, oblong, rectangular, square, or polygonal opening in first rod 72.

Figure 2C:
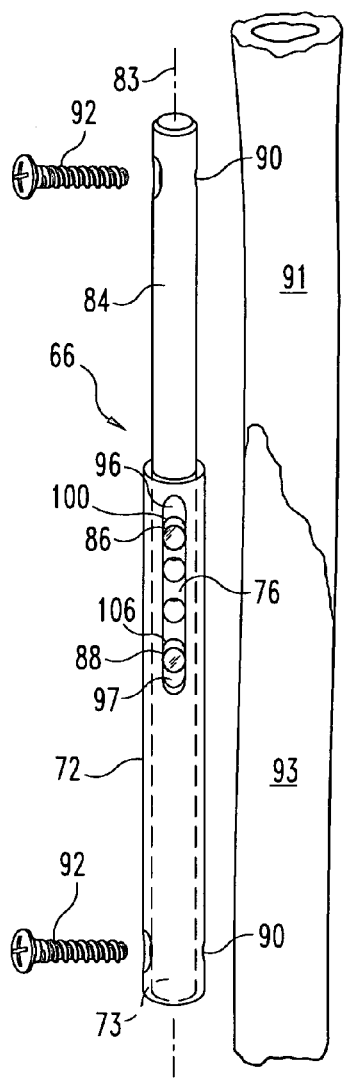
FIG. 2c is a perspective view of still another embodiment of an orthopedic device having a two-part telescoping elongate member in accordance with the present invention.

FIG. 2c is perspective view illustrating the orthopedic device 64 in position to be secured to bone portion 91 and a second bone portion 93. As can be seen from the figure, a first restricting component 86 has been inserted into a first opening 100 and a second restricting component 88 has been inserted into a second opening 106. In this embodiment, the orthopedic device 64 inhibits rotation of first rod 72 in relation to second rod 84. Similarly, device 64 inhibits rotation of first bone portion 91 in relationship to second bone portion 93. Additionally, it can be observed from the gap 96 in slot 76 above restricting component 86 and a corresponding gap 97 below restricting component 88 that second rod 84 can still travel to a limited degree within the lumen 72 of first rod 72. This permits limited movement of first bone portion 91 in conjunction to second bone portion 93 when the two bone portions are attached to first rod and second rod 72 and 84, respectively.

As has been described above, it will be understood that in alternative embodiments gaps 96 and 97 can be eliminated by the selective sizing of slot 76 and/or selective placement of one or more restricting components 86 and/or 88. In this embodiment, first rod 72 and second rod 84 are not free to move either translationally or rotationally with respect to each other. Similarly, first bone portion 91 and second bone portion 93 are not free to move relative to each other.

In use, after implantation, the restricting components 86 and/or 88 begin to erode or degrade. When restricting components 86 and/or 88 have been either partially degraded and/or fully degraded, second rod 84 is permitted to either rotate and/or traverse within lumen 73 of first rod 72. This in turn allows translation and/or rotation of first bone portion 91 relative to second bone portion 93. Preferably, first rod 72 and second rod 84 remain secured to bone portions 91 and 93, respectively. Since second rod 84 remains within lumen 73 of first rod 72, bone portions 91 and 93 cannot completely separate from each other, thus preventing re-injury to the previous bone defect. Consequently, the orthopedic device 64 continues to restrict either rotational and/or translation movement of the first bone portion 91 relative to the second bone portion 93.

FIG. 3a is a perspective view of orthopedic device 100 in accordance with the present invention. Device 100 includes an elongate member 101 comprising a telescoping assembly of a first rod 110 and a second rod 120. Rods 110 and 120 can be provided substantially as described for rods 72 and 82 except as further discussed below. First rod 110 includes a lumen 111 extending at least partly therethrough in the longitudinal direction. Second rod 120 is slidably disposed within lumen 111 of first rod 110. As illustrated, rod 120 includes an opening 114 through which a bone fastener can be inserted. Similarly, second rod 120 includes an opening 115 through which a bone fastener can be inserted. It will be understood that the term "bone fastener" can be any orthopedic fastener known in the art, including glues, staples, bone screws, hooks, and the like.

The first rod 110 and the second rod 120 are operatively linked together by a restricting component 130. Restricting component 130 is provided in the form of a loop 131 that is fixedly attached to second rod 120 and first rod 110. Restricting component 130 initially inhibits translational and/or rotational motion of first rod 110 relative to second rod 120. Restricting component 130 may be comprised of a biodegradable material as described more fully below. In vivo, restricting component 130 biodegrades. As the restricting component degrades, the range of motion of first rod 110 relative to second rod 120 increases. Similarly, the rotational and/or translational motion of bone portions attached to first rod 110 and second rod 120 also increases.

FIG. 3b is a perspective view of an alternative embodiment of an orthopedic device 102 according to the present invention. Device 102 includes an elongate member or assembly 103 that comprises a first rod 116, a second rod 126, and at least one restricting component 130. At least a portion of a second rod 126 is slidably disposed within first rod 116. Initially, first rod 116 and second rod 126 are connected by restricting component 130, illustrated as loop 131. Loop 131 can comprise either a biodegradable material described below or a non-biocompatible material. Further, loop 131 can be either flexible or non-flexible. In the illustrated embodiment, a first end 132 of loop 131 is attached to first rod 116. This attachment can be accomplished by welding, gluing, over molding, and the like to secure end 132 to the side of rod 116. In the alternative, first end 132 can be received within a receptacle formed in the side of rod 116. A second end 133 of loop 131 can be similarly secured or attached to second rod 126. The distal ends of both rods 126 and 116 include openings 119 and 120, respectively, for attaching device 102 to bone portions using any bone fasteners known in the art.

First rod 116 also includes receptacle 80 formed therein. Receptacle 80 is illustrated as a slot 81 extending substantially parallel to the longitudinal axis of rod 116. In alternative embodiments, receptacle 80 can be formed as described above for slot 76. In still other embodiments, receptacle 80 can be provided as a round, oblong, rectangular, square, or polygonal opening in first rod 116.

Receptacle 80 can be sized as desired and/or selected depending upon the intended application, method of treatment, and type of tissue defect and the like. In the illustrated embodiment, receptacle 80 is sized to allow a gap 85a above pin 87 and a gap 85b below pin 87. This permits initial limited translational movement of second rod 126 to travel within lumen 113. The limited "travel" of rod 126 within lumen 113 can be further restricted or eliminated depending upon the length and placement of loop 131.

Second rod 126 can be provided substantially as described above for second rod 120 of device 100.

A second restricting component 86 is positioned in receptacle 80. Second restricting component 86 can be provided as a plug or pin 87. Second restricting component 86, similar to first restricting component 130, can be composed of either a biodegradable or a biostable material.

In one embodiment both pin 87 and loop 131 may be made of the same material, and may be sized so as to fully biodegrade at the same time. In another embodiment pin 87 and loop 131 may be formed of different materials, made in different thickness, or treated differently so that loop 131 and pin 87 have differing biostabilities and therefore contribute to the stability of device 102 within different time frames. In still another embodiment, pin 87 is formed of a biostable material, while loop 131 is comprised of a biodegradable material. As pin 87 biodegrades, the restriction imposed on the rotational, or translational, or both rotational and translational movement of first rod 116 and the second rod 126 relative to one another is reduced and eventually eliminated. However, loop 131 continues to further restrict the movements of first rod 116 and second rod 126 relative to one another, and, consequently, the bone portions to which they are attached.

It should be understood that any combination of restricting components such as loop 131 and pin 87 or a plurality of pins and loops having differing biostabilities are intended to be within the scope of the invention.

FIG. 3c illustrates an alternative embodiment of an orthopedic rod device 104 according to the present invention. Device 104 is formed similarly to device 102 and, consequently, the same reference numbers are used to denote like components. In this embodiment, first rod 117 is provided with an inner surface 82 in lumen 94 that restricts the degree of slidable travel of second rod 126. Surface 82 is illustrated as the bottom of lumen 89. The translational, or rotational or both the translational and rotational movement of rods 117 and 126 relative to one another may be further restricted by any of the means already discussed, for example, a bioabsorbable loop 131 or pin 87 disposed within receptacle 80 in the side of rod 117 and any combination of similar restricting components thereof, where at least one of the restricting components is biodegradable. It should also be understood that any element, for example a lip, edge, pin, screw or the like, operatively positioned on the lumen 94 of first rod 117 in the slidable path of second rod 126 may be used to restrict the slidable travel of second elongate member 126 within first elongate member 117.

Additionally, the lumen 94 of first rod 117 can have differing internal diameters or a gradually tapering internal diameter that restricts movement of second rod 126. In still yet other embodiments, second rod 126 can be formed to include a lip, edge, pin, screw, or the like to inhibit its movement relative to the first rod 117.

Figure 4A:
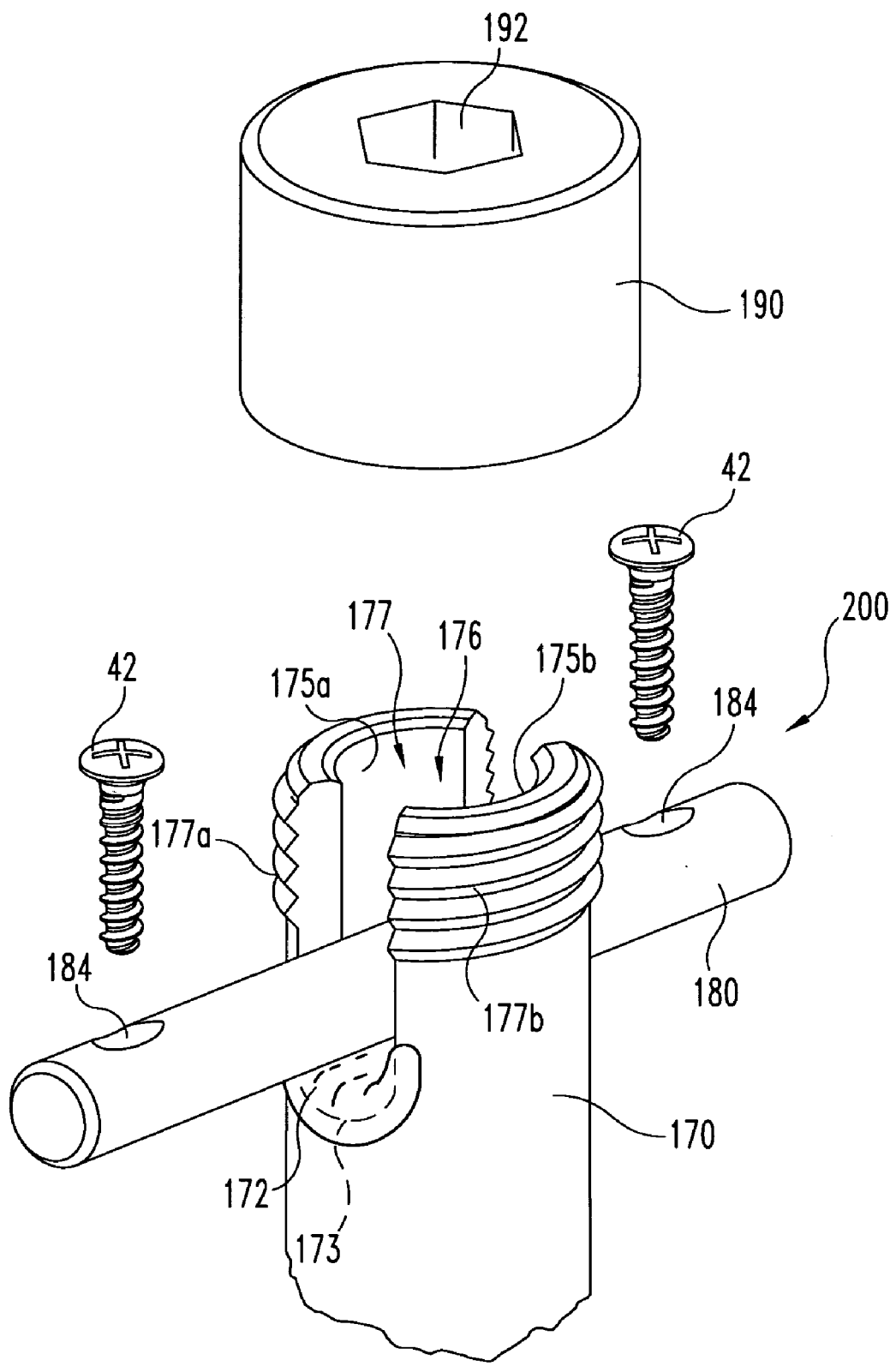
FIG. 4a is a perspective view of an embodiment of an orthopedic interconnection device comprising an anchoring body and an attached elongate member in accordance with the present invention.

FIG. 4a is a perspective view of orthopedic device 200 according to the present invention. Orthopedic device 200 can be provided as an interconnection element for use with a spinal rod system. Orthopedic device 200 includes a body 170 having a pair of arms 175a and 175b extending therefrom in a substantially parallel arrangement. Arms 175a and 175b define a receptacle 176 therebetween. In the illustrated embodiment, receptacle 176 can be viewed as a channel or trough formed in body 170. Consequently, receptacle 176 includes a bottom or cradle region 173 and an opposite, open end 177. An elongate rod 180 is disposed within receptacle 176. Additionally, a restricting component 172 is disposed in receptacle 176. In the illustrated embodiment, restricting component 172 is positioned adjacent cradle region 173. Consequently, restricting component 172 is positioned between rod 180 and body 170.

A cap 190 is provided to engage arms 175a and 175b to secure elongate rod 180 and restricting component 173 within receptacle 176. Cap 190 can include internal threads (not shown) that can engage with the external threads on first arm 175a and second arm 175b. Cap 190 can include a tool-engaging aperture, such as hex imprint 192. Other means for engaging a tool to cap 190 are also contemplated for the present invention. Consequently, cap 190 can be used to clamp body 170, rod 180, and restricting component 172 together.

Restricting component 172 can be formed of a biodegradable material discussed more fully below. Positioning restricting component 172 between elongate rod 180 and body 170 initially inhibits the translational or rotational or both the translational and rotational movement of elongate rod 180 relative to body 170. As discussed in previous embodiments, restricting component 172 can degrade in vivo. As the biodegradable material degrades, the force and/or frictional engagement between restricting component 172 and rod 180 decreases. Consequently, rod 180 is allowed translational and/or rotational movement relative to body 170. The further the biodegradable material erodes, the less the frictional engagement between restricting component 172 and rod 180. After the biodegradable material has completely eroded, elongate rod 180 is still retained within the receptacle 176. Consequently, rod 180 cannot be disengaged in vivo. After the biodegradable material has completely eroded, orthopedic device 200, which can be secured to two or more bone portions, still provides limited support and restricts movement of the two or more bone portions.

Figure 4B:
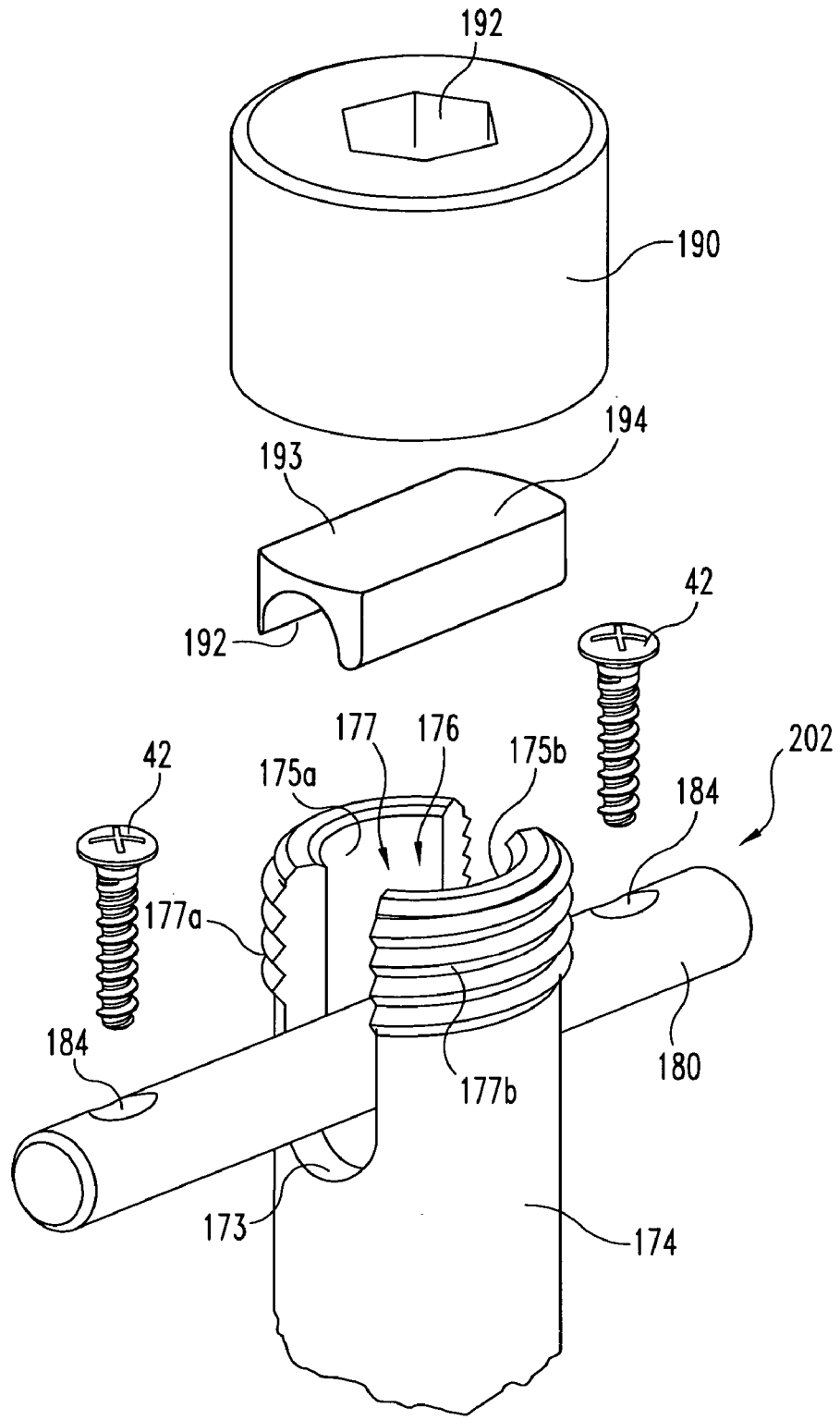
FIG. 4b is a perspective view of another embodiment of an orthopedic interconnection device comprising an anchoring body and an attached elongate member in accordance with the present invention.

FIG. 4b is a perspective view of an alternative embodiment of an orthopedic device 202. Orthopedic device 202 is structurally similar to orthopedic device 200. Consequently, same reference numbers will be used to denote like components. Orthopedic device 202 includes body 170 having first and second arms 175a and 175b defining a receptacle 176 therebetween. Elongate rod 180 and a restricting component 192 are also disposed within receptacle 176. In this embodiment, restricting component 192 is provided as a block 194 and positioned proximal to upper end 177 of receptacle 176.

Consequently, engaging cap 190 to first and second arms 175a and 175b forces restricting component 192 to engage rod 180. This induces a frictional engagement that restricts the relative movement of elongate rod 180 relative to body 170. Restricting component 192 can be formed of a biodegradable component, discussed more fully below. As noted in the earlier embodiments, as the biodegradable material erodes in vivo, the frictional engagement between restricting component 192 and elongate rod 180 decreases. This initially allows rod 180 to move either translationally and/or rotationally relative to body 170.

Figure 4C:
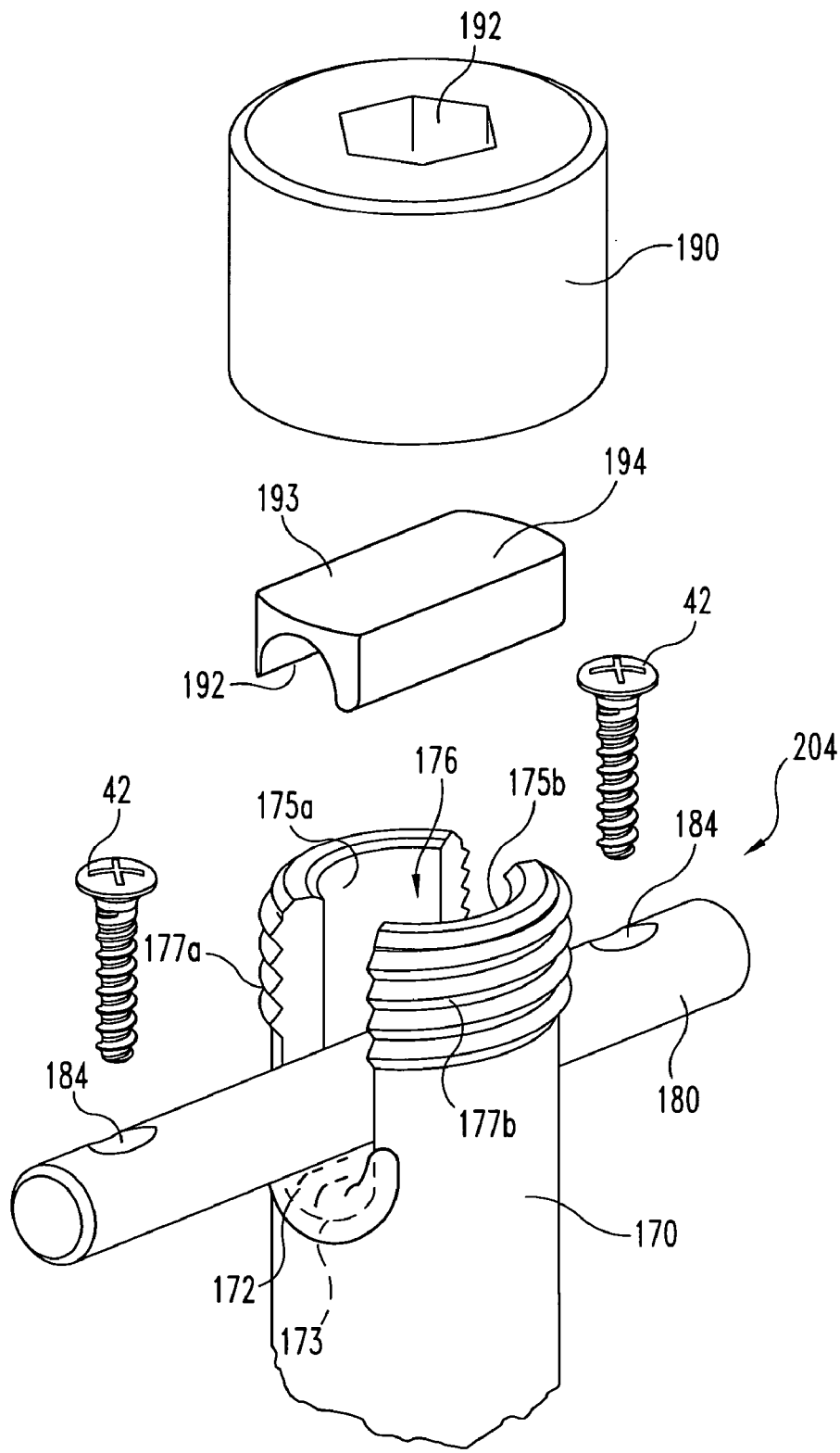
FIG. 4c is a perspective view of still another embodiment of an orthopedic device comprising an anchoring body and an attached elongate member in accordance with the present invention.

FIG. 4c is a perspective view of yet another embodiment of an orthopedic device 204 in accordance with the present invention. Orthopedic device 204 is provided substantially as has been described for orthopedic devices 200 and 202. Consequently, the same reference numbers will be used to denote like components. In this embodiment, orthopedic device 204 includes a first restricting component 172 and a second restricting component 192. Both first and second restricting component 172 and 192 are disposed within receptacle 176. In the illustrated embodiment, restricting component 172 is disposed in the cradle region 173 and second restricting component 192 is disposed proximal to upper end 177 between elongate member 180 and cap 190. Engaging cap 190 to first and second arms 175a and 175b forces the first and second restricting components 172 and 192 to engage with rod 180 and body 170. This induces a frictional engagement that inhibits or restricts movement of rod 180 within receptacle 176. As noted before, restricting component 172 and/or restricting component 192 or both can be formed of a biodegradable material. It will be understood that restricting component 172 can comprise a first biodegradable material. Restricting component 192 can comprise a second biodegradable material that is the same or different from the first biodegradable material. Consequently, the degradation rate of first restricting component 172 can be the same or different from that of the degradation rate of the second restricting component 192. Furthermore, restricting component 172 and restricting component 192 can be sized to have different thicknesses or treated differently so that they have differing biostability or erode at different rates or within different time frames. Additionally, one of either restricting component 172 and restricting component 192 can be formed of a biostable material that does not appreciably erode or disintegrate in vivo.

Figure 5:
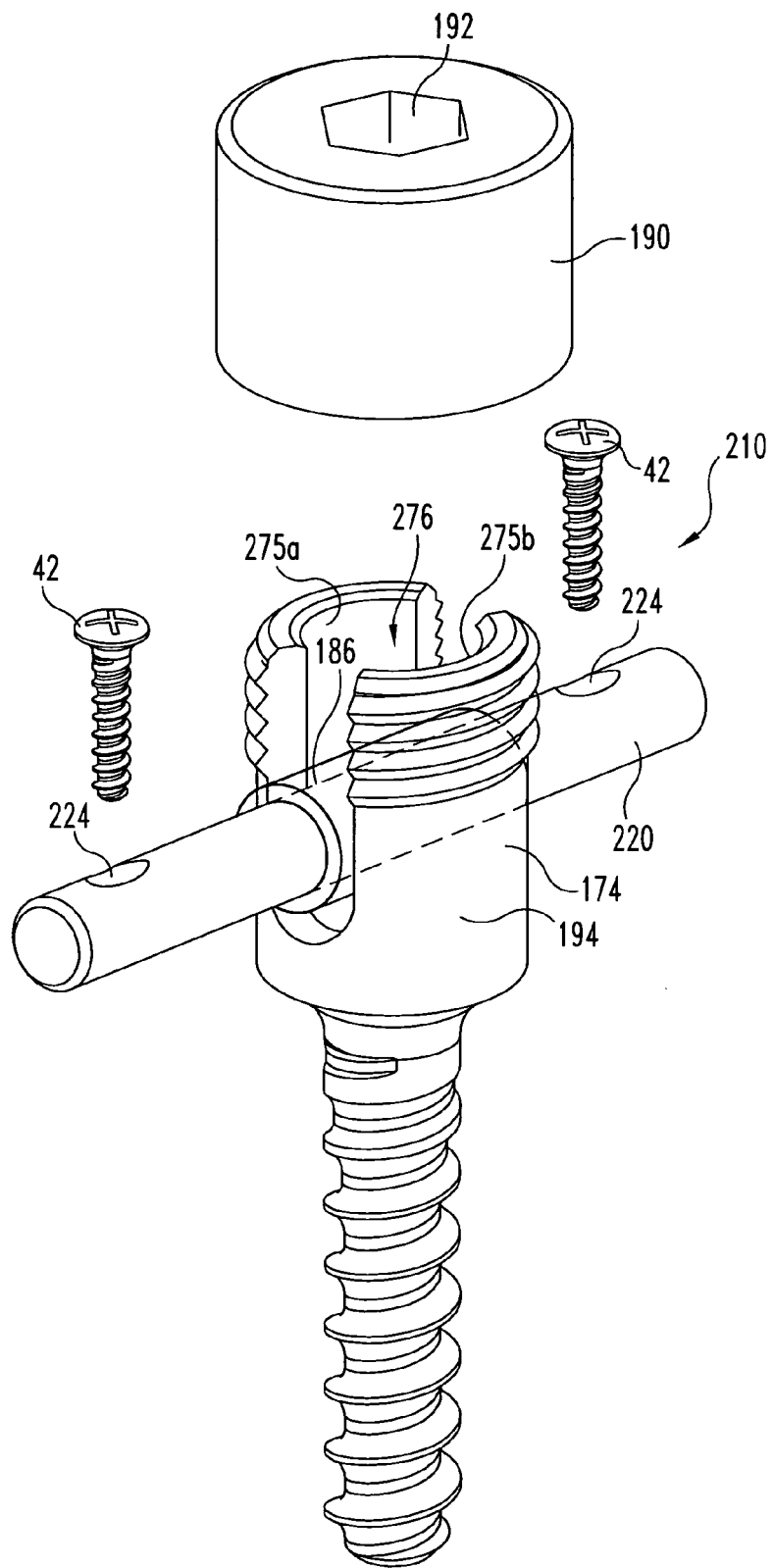
FIG. 5 is a perspective view of an embodiment of an orthopedic interconnection device comprising a pedicle screw, an attached elongate member, and a restricting component in accordance with the present invention.

FIG. 5 is a perspective view of another embodiment of an orthopedic device 210 in accordance with the present invention. Device 210 is illustrated as a pedicle screw 174. Pedicle screw 174 include an interconnection body 194 having a receptacle 276 formed therein. Additionally, an elongate rod 220 and a restricting component 186 are disposed within receptacle 276. In the illustrated embodiment, restricting component 186 is provided as a sleeve 187 that partially or completely surrounds a portion of rod 220. Restricting component 186 comprises a biodegradable material discussed more fully below. Cap 190 can be provided to engage onto first and second arms 275a and 275b to secure body 194, rod 220, and restricting component 186 together. This effectively inhibits relative translational and/or rotational movement of rod 220 relative to body 194. Since restricting component 186 is formed of a biodegradable material, which is discussed more fully below, in vivo the biodegradable material erodes or degrades. The degradation of the biodegradable material allows the captured rod 220 limited translational and/or rotational movement. As with other embodiments, since rod 220 can be secured to a first and second bone portion, this also allows a relative translational or rotational movement of the respective bone portions.

Figure 6:
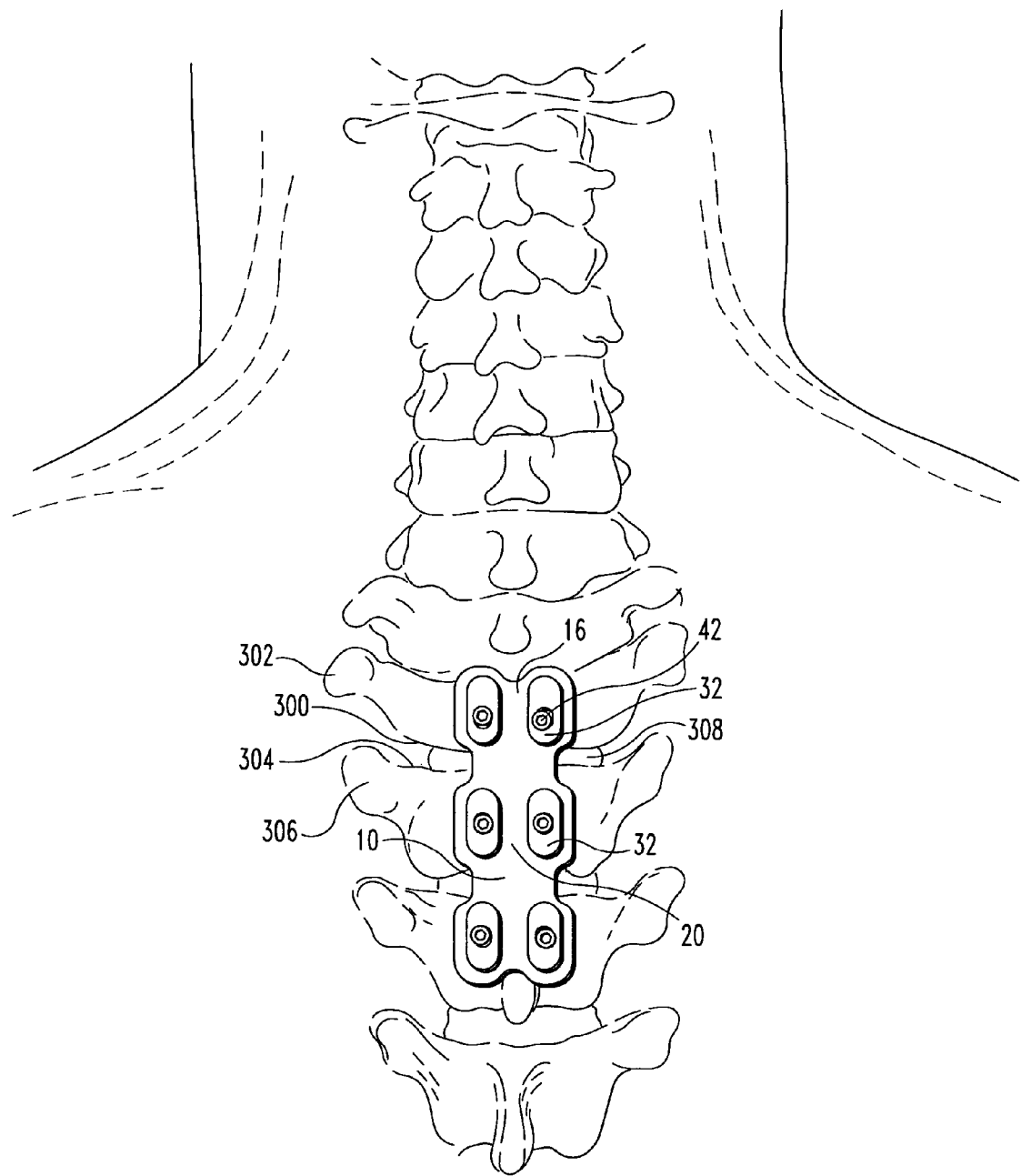
FIG. 6 is a plan view illustrating one embodiment of a method of treating the spine by attaching a bone plate having bioabsorbable restricting components in accordance with the present invention.

In use, any of the orthopedic devices 10, 12, 14, 62, 64, 100, 102, 104, 200, 202, 204, and 210 can be used to secure and treat bone defects. For example, as illustrated in FIG. 6, orthopedic device 10 can be used to treat a spinal defect. In this specific illustration, the spinal defect occurs either on the inferior end plate 300 of vertebra 302 and/or the superior end plate 304 of vertebra 306, or both. The surgeon can perform either a full or partial discectomy if desired and if the defect occurs in the nucleus pulposa and/or spinal disc structure. The discectomy can include either replacing the disc with a disc prosthesis and/or inserting a spinal spacer between the affected vertebrae, which spinal spacer can include an osteogenic material to induce bone fusion or not, as desired.

Referring to FIG. 6, bone orthopedic device 10 is affixed to the spine using two or more bone fasteners 42. In this embodiment, bone fasteners 42 are embedded in the restricting component 32. Initially device 10 maintains the desired disc space height 308 and maintains vertebrae 302 and 306 in a rigid confirmation relative to one another. As biodegradable restricting component 32 degrades, the range of motion available to vertebra 302 and 304 relative to one another increases. This in effect allows the two vertebrae to exert increasing amounts of force on new bone tissue growing between the vertebrae.

The biodegradable component included in one or more of the restricting components describe herein can be formed or composed of a variety of rigid materials including, without limitation, resorbable polymeric materials, resorbable composite materials, and resorbable ceramic materials.

In preferred embodiments, the material selected to provide the structural features of the elongate member, the bone plates, the elongate rods, and interconnection elements include resilient materials such as, without limitation, nitonal, titanium, titanium-vanadium-aluminum alloy, cobalt-chromium alloy, cobalt-chromium-molybdenum alloy, cobalt-nickel-chromium-molybdenum alloy, biocompatible stainless steel, tantalum, niobium, hafnium, tungsten, and alloys thereof; reinforced polymeric materials, carbon poly(ether, ether, ketone) (PEEK), poly(aryl ether, ketone) (PAEK), and the like. Consequently, if desired, bridge portion 25 exhibits an elastic property and preferably performs analogous to a series of leaf springs stacked on top of each other.

In one embodiment, the biodegradable material 14 can include polymeric materials formed from oligomers, homopolymers, copolymers, and polymer blends that include polymerized monomers derived from l, d, or d/l lactide (lactic acid); glycolide (glycolic acid); ethers; acids; anhydrides; olefins, such as ethylene, propylene, butene-1, pentene-1, hexene-1,4-methylpentene-1, styrene, norbornene and the like; butadiene; polyfunctional monomers such as acrylate, methacrylate, methyl methacrylate; esters, for example, caprolactone and hydroxy esters; and mixtures of these monomeric repeating units. Specific examples of biodegradable polymeric materials for use in the present invention include poly(l,d-lactide) (PLDLA).

Use of the term "copolymers" is intended to include within the scope of the invention polymers formed of two or more unique monomeric repeating units. Such copolymers can include random copolymers; graft copolymers; body copolymers; radial body, dibody, and tribody copolymers; alternating copolymers; and periodic copolymers. Use of the term "polymer blend" is intended to include polymer alloys, semi-interpenetrating polymer networks (SIPN), and interpenetrating polymer networks (IPN).

In a preferred embodiment, the biodegradable material 14 comprises a biodegradable polymeric material including: poly(amino acids), polyanhydrides, polycaprolactones, poly(lactic-glyclolic acid), polyhydroxybutyrates, polyorthoesters, and poly(d,l-lactide).

In other embodiments, the biodegradable material can comprise biodegradable ceramic materials and ceramic cements. Examples of biodegradable ceramic materials include: hydroxy apatite, hydroxyapatite carbonate, corraline, calcium phosphate, tricalcium phosphatem, and hydroxy-apatate particles. Examples of biodegradable ceramic cements include calcium phosphate cement. Such calcium phosphate cements are preferably synthetic calcium phosphate materials that include a poorly or low crystalline calcium phosphate, such as a low or poorly crystalline apatite, including hydroxyapatite, available from Etex Corporation and as described, for example, in U.S. Pat. Nos. 5,783,217; 5,676,976; 5,683,461; and 5,650,176, and PCT International Publication Nos. WO 98/16268, WO 96/39202 and WO 98/16209, all to Lee et al. Use of the term "poorly or low crystalline" is meant to include a material that is amorphous, having little or no long range order and/or a material that is nanocrystalline, exhibiting crystalline domains on the order of nanometers or Angstroms.

In other embodiments, the biodegradable material can be formed of composite materials. Examples of composite materials include as a base material or matrix, without limitation: ceramics, resorbable cements, and/or biodegradable polymers listed above. Each of the base materials can be impregnated or interspersed with fibers, platelets, and particulate reinforcing materials.

In one form, the biodegradable material comprises a resorbable, moldable material that can be molded at an elevated temperature and then allowed to set up into a hardened material at around body temperature, such as the material sold under the trade name BIOGLASS® discussed in WO 98/40133, which is incorporated by reference herein.

The restricting components of the present invention can be tailored to degrade at a predetermined or pre-selected rate by suitably selecting the size, thickness, and/or restricting component. In preferred embodiments, the biodegradable material degrades at a rate comparable to the new bone in-growth into the bone defect or bone fusion site. In particularly preferred embodiments, the restricting component has an in vivo half life of greater than three months, more preferably the in vivo half life of the restricting component is greater than six months; still more preferably the in vivo half life is greater than one year. By use of the term "half life", it is understood that the degradation rate of the restricting component is such that the restricting component loses half of its initial mass in vivo, presumably due to resorption, degradation, and/or elimination.

In addition or in the alternative, it may be desirable to promote bone fusion between the adjacent vertebrae or between any bone portions on either side of a bone defect. In this embodiment, it may be desirable to include an osteogenic material or a bone growth material such as an osteoinductive or an osteoconductive material. For example, it may be desirable to introduce a osteogenic factor such as a bone morphogenic protein (BMP). Examples of bone growth materials include an osteoinductive factor, such as an osteoinductive protein or a nucleotide or a nucleotide sequence encoding an osteoinductive protein operably associated with a promoter (e.g., provided in a vector such as a viral vector), for example a bone morphogenetic protein or a gene encoding the same operationally associated with a promoter which drives expression of the gene in the animal recipient to produce an effective amount of the protein. The bone morphogenic protein (BMP) in accordance with this invention is any BMP able to stimulate differentiation and function of osteoblasts and osteoclasts. Examples of such BMPs are BMP-2, BMP-4, and BMP-7, more preferably rhBMP-2 or rhBMP-7, most preferably, rhBMP-2. Purified recombinant BMPs are preferred for use in the inventive compositions for their provision of high osteoinductive potentials. BMP gene sequences and methods for producing recombinant and naturally-derived BMPs are known in the art, and for additional information on this subject reference may be made, for instance, to U.S. Pat. Nos. 5,108,753; 5,187,076; 5,366,875; 4,877,864; 5,108,922; 5,116,738; 5,013,649; 5,106,748; and 4,294,753; and International Publication Nos. WO93/00432; WO94/26893; and WO94/26892. The osteoinductive factor may also be LIM mineralization protein (LMP) or a suitable vector incorporating a gene encoding the same operably associated with a promoter, as described in WO99/06563 (see also genbank accession No. AF095585). When such vectors are employed as osteogenic factors in accordance with the invention, they are preferably delivered in conjunction with cells, for example autologous cells from the recipient of the implant. Most preferably the vector is delivered in conjunction with autologous white blood cells derived from bone marrow or peripheral blood of the recipient.

The osteogenic factor will be incorporated in an amount which is effective to stimulate the formation of bone within the animal recipient. In more preferred compositions incorporating protein osteogenic factors, the osteogenic factor will be incorporated in a weight ratio of about 1:100 to about 1:1000 relative to the overall composition, more preferably about 1:100 to about 1:500. As will be understood, when the osteogenic factor comprises a nucleotide sequence, sufficient amounts of the delivery vehicle (vector) will be incorporated to cause significant transduction of cells, so as to cause the generation of sufficient protein at the site to induce bone formation.

Additionally, or in the alternative, the present invention can be used with one or more of the devices disclosed in co-pending U.S. patent application Ser. No. 10/690,451 filed on Oct. 21, 2003 and entitled "Dynamizable Orthopedic Implants and Their Use in Treating Bone Defects", which is hereby incorporated by reference in its entirety.

While the invention has been illustrated and described in detail in the drawings and foregoing description, the same is considered to be illustrative and not restrictive in character, it is understood that only the preferred embodiments have been shown and described and that all changes and modifications that come within the spirit of the invention are desired to be protected. Any reference to a specific directions, for example, references to up, upper, down, lower, and the like, is to be understood for illustrative purposes only or to better identify or distinguish various components from one another. These references are not to be construed as limiting in any manner to the orthopedic device and/or methods for using the orthopedic device as described herein.

Further, all publications, patents, and patent applications cited in this specification are herein incorporated by reference as if each individual publication, patent, or patent application was specifically and individually indicated to be incorporated by reference and set forth in its entirety herein.

Unless specifically identified to the contrary, all terms used herein are used to include their normal and customary terminology. Further, while various embodiments of medical devices having specific components and structures are described and illustrated herein, it is to be understood that any selected embodiment can include one or more of the specific components and/or structures described for another embodiment where possible.

Further, any theory of operation, proof, or finding stated herein is meant to further enhance understanding of the present invention and is not intended to make the scope of the present invention dependent upon such theory, proof, or finding.

What is claimed is:

1. An orthopedic implant comprising:
   a bone plate having a top surface and an opposed bottom surface, said bottom surface for lying adjacent to bone, said bone plate including an opening therethrough from said top surface to said bottom surface, said opening having an area of a first dimension;
   a biodegradable restricting component disposed at least partially in said plate opening, said restricting component defining an opening within and through said area, said opening of said restricting component having a second dimension smaller than said first dimension; and
   a fastener having a portion configured to anchor to bone, said fastener portion extending through said opening of said restricting component and said opening of said bone plate, said fastener portion having a width dimension that is substantially the same as the second dimension of the opening of said restricting component, said width dimension being smaller than said first dimension of said area;
   wherein at the time of implantation said restricting component inhibits motion of said fastener with respect to said plate in a first direction, and an edge of said opening of said bone plate inhibits motion of said fastener in a second direction opposite from the first direction; and
   wherein after said restricting component has degraded, said fastener remains restricted from motion in the second direction, but is uninhibited from motion within said opening in said bone plate in the first direction.

2. The device of claim 1, wherein said plate comprises a biocompatible metal.

3. The device of claim 1, wherein said plate comprises an elastic material.

4. The device of claim 1, wherein said plate comprises a material selected from the group consisting of: nitinol, titanium, titanium-vanadium-aluminum alloy, cobalt-chromium alloy, cobalt-chromium-molybdenum alloy, cobalt-nickel-chromium-molybdenum alloy, biocompatible stainless steel, tantalum, niobium, hafnium, tungsten, poly(ether, ether ketone), poly(aryl, ether, ketone).

5. The device of claim 1, wherein said restricting component completely biodegrades within two years while said elongate member remains engaged to the said two or more bone portions.

6. The device of claim 1, wherein said restricting component is provided to have an initial mass and wherein the restricting component degrades in vivo to less than half its initial mass within one year.

7. The device of claim 1, wherein said restricting component is provided to have an initial mass and wherein in vivo the restricting component retains greater than half its initial mass for a time period of greater than one year.

8. The device of claim 1, wherein said biodegradable restricting component composes a material selected from a group consisting of: poly(amino acids), polyanhydrides, polycaprolactones, polylactates, polyglycolates, poly(lactic-glycolic acid), polyorthoesters, and blends thereof.

9. The device of claim 1, wherein the restricting component is disposed in said plate opening so that said restricting component opening is substantially centered in said plate opening.

10. The device of claim 1, wherein the restricting component is disposed in said plate opening so that said restricting component opening is closer to one end of said plate opening.

11. The device of claim 1, wherein said bone plate includes a plurality of openings therethrough from said top surface to said bottom surface, each said opening having an area with a respective first dimension, and each of said openings having a respective biodegradable restricting component disposed at least partially therein, each said restricting component at least partially defining an open portion of said area of its respective opening, said open portions each having a respective second dimension smaller than said first dimension of its respective opening area, and wherein each said opening has a respective fastener extending through the respective restricting component and opening, each said fastener having a width dimension that is substantially the same as the respective second dimension of the open area portion at least partially defined by the respective restricting component, said respective width dimension being smaller than said first dimension of the respective area.

12. The device of claim 11, wherein the restricting components degrade at substantially the same rate.

13. The device of claim 11, wherein at least one of said restricting components degrades at a rate different from a degradation rate of another of said restricting components.

14. The device of claim 1, wherein said fastener is a bone screw.

15. The device of claim 1, wherein said restricting component is both within said opening and outside said opening in contact with said top surface.

16. The device of claim 1, wherein said plate has at least one additional opening, and further comprising a second fastener extending through said at least one additional opening, and wherein at the time of implantation there is no synthetic material between said second fastener and said plate.

* * * * *